US006365688B1

(12) United States Patent
Andell et al.

(10) Patent No.: US 6,365,688 B1
(45) Date of Patent: Apr. 2, 2002

(54) ORGANOMETALLIC COMPOUND, PREPARATION METHOD THEREOF AND PROCESS FOR POLYMERIZATION OF OLEFINS BY MEANS OF A CATALYST COMPOSITION INCLUDING THE ORGANOMETALLIC COMPOUND

(75) Inventors: Ove Andell, Helsinki; Janne Maaranen, Vantaa, both of (FI)

(73) Assignee: Borealis Technology Oy, Porvoo (FI)

( * ) Notice: Subject to any disclaimer, the term of this patent is extended or adjusted under 35 U.S.C. 154(b) by 0 days.

(21) Appl. No.: 09/445,956

(22) PCT Filed: Aug. 21, 1998

(86) PCT No.: PCT/FI98/00644

§ 371 Date: Dec. 16, 1999

§ 102(e) Date: Dec. 16, 1999

(87) PCT Pub. No.: WO99/10353

PCT Pub. Date: Mar. 4, 1999

(30) Foreign Application Priority Data

Aug. 22, 1997 (FI) .................................................. 973451

(51) Int. Cl.$^7$ .................................................. C08F 4/42
(52) U.S. Cl. .................. 526/160; 526/348; 526/153; 526/159; 526/141; 526/147; 526/164; 526/160; 526/943; 502/123; 502/152
(58) Field of Search ................. 526/348, 161, 526/153, 159, 141, 147, 164, 160, 943; 502/123, 152

(56) References Cited

FOREIGN PATENT DOCUMENTS

| DE | 2735286 A1 | 2/1979 |
| EP | 0082415 A1 | 6/1983 |
| FR | 1519948 | 2/1968 |
| WO | 95/35164 | 12/1995 |

OTHER PUBLICATIONS

Oberthur et al. Chem. Ber. 129, 1087–1091, 1996.*
Bear et al. Inorg. Chem., 35, 1395–1398, 1996.*
Chem. Ber., vol. 129, 1996, Markus Oberthur et al., pp. 1087–1091.
Chemical Abstracts, vol. 127, No. 18, Nov. 3, 1997, Abstract No. 248532.
Journal of the American Chemical Society, vol. 92, No. 17, Aug. 1970 pp. 5118–5126.
Chemical Abstracts 125:236828, 1997, "Complexes of CU(II), Ni(II) and Co(II) with Schiff base derived from salicylaldehyde . . . ".

* cited by examiner

Primary Examiner—David W. Wu
Assistant Examiner—Ling-Siu Choi
(74) Attorney, Agent, or Firm—Birch Stewart Kolasch & Birch, LLP.

(57) ABSTRACT

The invention relates to an organometallic compound comprising a central transition metal atom and a ligand coordinated thereto having a heteroatomic ring structure, characterized in that the ligand includes at least three nitrogen atoms, three of them being bonded to the same carbon atom.

20 Claims, No Drawings

ORGANOMETALLIC COMPOUND, PREPARATION METHOD THEREOF AND PROCESS FOR POLYMERIZATION OF OLEFINS BY MEANS OF A CATALYST COMPOSITION INCLUDING THE ORGANOMETALLIC COMPOUND

This application is the national phase under 35 U.S.C. § 371 of PCT International Application No. PCT/FI98/00644 which has an International filing date of Aug. 21, 1998, which designated the United States of America.

The patent application relates to an organometallic compound comprising a central transition metal atom and a ligand coordinated thereto having a heteroatomic ring structure, a process for its preparation and a process for polymerization of olefins by means of catalyst compositions including said organometallic compounds.

For single active site olefin polymerizations is traditionally used organometallic compounds wherein a central transition metal atom is coordinated by one or more aromatic rings and optionally other groups which may be organic or halide groups, preferably alkyl or chloride groups. The aromatic rings have π-electrons by which the coordination to the metal is completed. Five members for the ring are most often used, and then the compounds are many times named as metallocenes. These cyclopentadienyl groups can be substituted in many ways: carbon atoms of the ring are connected by one or more separate groups which may contain heteroatoms and/or they can form one or more other rings. Fused rings connected to the cyclopentadienyl ring may constitute even very complicated compound structures. The cyclopentadienyl ring or its replacement rings with their fused rings may contain in their ring structure one or more heteroatoms, too.

This application relates in particular to the heteroatomic ring structure. Characterizing for the structure is that a ligand of the central transition metal atom includes at least three nitrogen atoms and essentially three nitrogens of them are bonded to the same central carbon atom forming a structure wherein the carbon atom is surrounded in three directions by the three nitrogens.

The structure of the organometallic compound may preferably be presented by the formula (1)

$$L_n M X_{m-n} \tag{1}$$

wherein at least one L denotes said ligand coordinated by a π-electron bond to M and includes a heterocyclic ring structure having at least two fused rings and at least three nitrogen atoms, three of them being connected to said same carbon atom, one of them being common for two rings and two of them being in separate rings, M is the central transition metal atom and belongs to Groups IV, V or VI of the Periodic Table of the Elements, X is an organic group or a halide coordinated to said central transition metal atom M, m signifies the coordination (ligand) number of said transition metal atom M, and n signifies an integer from 1 to m.

The ligand L, except one ligand according to the invention, may be also a cyclopentadienyl ring or its substituted derivative, or the ligand may be also a different kind of group, aromatic or not by its nature. Between the ligands can be a bridge group.

The inventional structure for the ligand (L) is preferably presented in the equation (2):

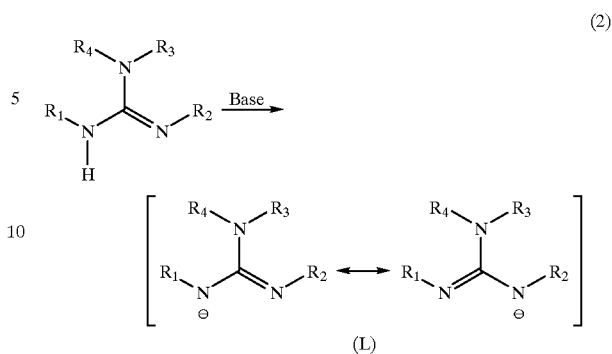

where groups $R_1$, $R_2$, $R_3$ and $R_4$ are the same or different selected from the group of H, $C_1$–$C_{12}$ alkyl, alkenyl, aryl (phenyl preferable), alkylaryl, or the groups $R_1$, $R_2$, $R_3$ and $R_4$ may contain silicon atoms instead of one or more carbon atoms, preferably they are $SiH_3$, $SiH_2R_5$, $SiHR_6R_7$, $SiR_8R_9R_{10}$ groups where groups $R_5$ to $R_{10}$ are also the groups recited above. The substituent groups may be also a combination of several groups recited above. The $R_1$ to $R_4$ can be interconnected to another one to form bridged structures. In the presence of a base a balance exists in the formula (2) between two ionic isomeric structures which are presented in the right of the formula (2). L is preferably a triaza bicyclo alkenyl, more preferably a 1,5,7-triazabicyclodec-5-enyl, most preferably a 1,5,7-triaza{4.4.0}bicyclodec-5-enyl.

Several compounds according to the invention are recited in a list below and they can be prepared in a similar method using proper reagents instead of those used in the TAB preparation and in the preparation of the inventional metallocene compounds including the ligand.

(1,5,7-triaza[4.4.0]bicyclo-dec-5-enyl)zirconium trichloride (3)
Tris(1,5,7-triaza[4.4.0]bicyclo-dec-5-enyl)zirconium chloride (4)
Bis(1,5,7-triaza[4.4.0]bicyclo-dec-5-enyl)zirconium dichloride (5)
Tetracis(1,5,7-triaza[4.4.0]bicyclo-dec-5-enyl)zirconium
(1,5,7-triaza[4.4.0]bicyclo-dec-5-enyl)titanium trichloride (2)
Tris(1,5,7-triaza[4.4.0]bicyclo-dec-5-enyl)titanium chloride
Bis(1,5,7-triaza[4.4.0]bicyclo-dec-5-enyl)titanium dichloride
Tetracis(1,5,7-triaza[4.4.0]bicyclo-dec-5-enyl)titanium
(1,5,7-triaza[4.4.0]bicyclo-dec-5-enyl)hafnium trichloride
Tris(1,5,7-triaza[4.4.0]bicyclo-dec-5-enyl)hafnium chloride
Bis(1,5,7-triaza[4.4.0]bicyclo-dec-5-enyl)hafnium dichloride
Tetracis(1,5,7-triaza[4.4.0]bicyclo-dec-5-enyl)hafnium
(1,5,7-triaza[4.4.0]bicyclo-dec-5-enyl)chromium dichloride
Tris(1,5,7-triaza[4.4.0]bicyclo-dec-5-enyl)chromium
Bis(1,5,7-triaza[4.4.0]bicyclo-dec-5-enyl)chromium chloride
(Dimethylamine)-(1,5,7-triaza[4.4.0]bicyclo-dec-5-enyl)zirconium dichloride
(Diethylamine)-(1,5,7-triaza[4.4.0]bicyclo-dec-5-enyl)zirconium dichloride
(Methyl-tertButyl-amine)-(1,5,7-triaza[4.4.0]bicyclo-dec-5-enyl)zirconium dichloride
(Dimethylamine)-(1,5,7-triaza[4.4.0]bicyclo-dec-5-enyl)titanium dichloride
(Diethylamine)-(1,5,7-triaza[4.4.0]bicyclo-dec-5-enyl)titanium dichloride (Methyl-tertButyl-amine)-(1,5,7-triaza[4.4.0]bicyclo-deatomc-5-enyl)titanium dichloride
(Dimethylamine)-(1,5,7-triaza[4.4.0]bicyclo-dec-5-enyl)hafnium dichloride
(Diethylatamine)-(1,5,7-triaza[4.4.0]bicyclo-dec-5-enyl)hafnium dichloride
(Methyl-tertButyl-amine)-(1,5,7-triaza[4.4.0]bicyclo-dec-5-enyl)hafnium dichloride
(Dimethylamine)-(1,5,7-triaza[4.4.0]bicyclo-dec-5-enyl)chromium chloride
(Diethylamine)-(1,5,7-triaza[4.4.0]bicyclo-dec-5-enyl)chromium
(Methyl-tertButyl-amine)-(1,5,7-triaza[4.4.0]bicyclo-dec-5-enyl)chromium chloride
Bis(1,5,7-triaza[4.4.0]bicyclo-dec-5-enyl)zirconium di(N,N-dimethylamide)
Tris(1,5,7-triaza[4.4.0]bicyclo-dec-5-enyl)zirconium (N,N-dimethylamide)
(1,5,7-triaza[4.4.0]bicyclo-dec-5-enyl)zirconium tri(N,N-dimethylamide)
Bis(1,5,7-triaza[4.4.0]bicyclo-dec-5-enyl)zirconium di(N,N-diethylamide)
Tris(1,5,7-triaza[4.4.0]bicyclo-dec-5-enyl)zirconium (N,N-diethylamide)
(1,5,7-triaza[4.4.0]bicyclo-dec-5-enyl)zirconium tri(,N-diethylamide)
Bis(1,5,7-triaza[4.4.0]bicyclo-dec-5-enyl)titanium di(N,N-dimethylamide)
Tris(1,5,7-triaza[4.4.0]bicyclo-dec-5-enyl)titanium (N,N-dimethylamide)
(1,5,7-triaza[4.4.0]bicyclo-dec-5-enyl)titanium tri(N,N-dimethylamide)
Bis(1,5,7-triaza[4.4.0]bicyclo-dec-5-enyl)titanium di(N,N-diethylamide)
Tris(1,5,7-triaza[4.4.0]bicyclo-dec-5-enyl)titanium (N,N-diethylamide)
(1,5,7-triaza[4.4.0]bicyclo-dec-5-enyl)titanium tri(N,N-diethylamide)
Bis(1,5,7-triaza[4.4.0]bicyclo-dec-5-enyl)hafnium di(N,N-diethylamide)
Tris(1,5,7-triaza[4.4.0]bicyclo-dec-5-enyl)hafnium (N,N-dimethylamide)
(1,5,7-triaza[4.4.0]bicyclo-dec-5-enyl)hafnium tri(N,N-dimethylamide)
Bis(1,5,7-triaza[4.4.0]bicyclo-dec-5-enyl)hafnium di(N,N-diethylamide)
Tris(1,5,7-triaza[4.4.0]bicyclo-dec-5-enyl)hafnium (N,N-diethylamide)
(1,5,7-triaza[4.4.0]bicyclo-dec-5-enyl)hafnium tri(N,N-diethylamide)
Bis(1,5,7-triaza[4.4.0]bicyclo-dec-5-enyl)chromium (N,N-dimethylamide)
(1,5,7-triaza[4.4.0]bicyclo-dec-5-enyl)chromium di(N,N-dimethylamide)
Bis(1,5,7-triaza[4.4.0]bicyclo-dec-5-enyl)chromium (N,N-diethylamide)
Tris(1,5,7-triaza[4.4.0]bicyclo-dec-5-enyl)chromium
(1,5,7-triaza[4.4.]bicyclo-dec-5-enyl)chromium di(N,N-diethylamide)
(Cyclopentadienyl)-(1,5,7-triaza[4.4.0]bicyclo-dec-5-enyl)zirconium dichloride
(n-Butyl-Cyclopentadienyl)-(1,5,7-triaza[4.4.0]bicyclo-dec-5-enyl)zirconium dichloride
(Indenyl)-(1,5,7-triaza[4.4.0]bicyclo-dec-5-enyl)zirconium dichloride
(Fluorenyl)-(1,5,7-triaza[4.4.0]bicyclo-dec-5-enyl)zirconium dichloride
(Cyclopentadienyl)-(1,5,7-triaza[4.4.0]bicyclo-dec-5-enyl)titanium dichloride
(n-Butyl-Cyclopentadienyl)-(1,5,7-triaza[4.4.0]bicyclo-dec-5-enyl)titanium dichloride
(Indenyl)-(1,5,7-triaza[4.4.0]bicyclo-dec-5-enyl)titanium dichloride
(Fluorenyl)-(1,5,7-triaza[4.4.0]bicyclo-dec-5-enyl)titanium dichloride
(Cyclopentadienyl)-(1,5,7-triaza[4.4.0]bicyclo-dec-5-enyl)hafnium dichloride
(n-Butyl-Cyclopentadienyl)-(1,5,7-triaza[4.4.0]bicyclo-dec-5-enyl)hafnium dichloride
(Indenyl)-(1,5,7-triaza[4.4.0]bicyclo-dec-5-enyl)hafnium dichloride
(Fluorenyl)-(1,5,7-triaza[4.4.0]bicyclo-dec-5-enyl)hafnium dichloride
(Cyclopentadienyl)-(1,5,7-triaza[4.4.0]bicyclo-dec-5-enyl)chromium chloride
(n-Butyl-Cyclopentadienyl)-(1,5,7-triaza[4.4.0]bicyclo-dec-5-enyl)chromium chloride
(Indenyl)-(1,5,7-triaza[4.4.0]bicyclo-dec-5-enyl)chromium chloride
(Fluorenyl)-(1,5,7-triaza[4.4.0]bicyclo-dec-5-enyl)chromium chloride The invention also relates to a method to prepare an organometallic compound comprising a central transition metal and a ligand coordinated thereto having a heteroatomic ring structure. The compound consisting of the ligand which includes at least three nitrogen atoms, three of them being bonded to the same carbon atom, and a hydrogen atom bound to one of said three nitrogen atoms of said ligand, is reacted with a metallocene and/or a halide of said transition metal. Preferably, an alkaline metal salt of the ligand is reacted with a transition metal halide, preferably chloride. According to an embodiment, the ligand is prepared as follows: first a salt of an alkaline metal of toluene is produced, and the salt is then reacted in toluene solution with said compound consisting of the ligand and a hydrogen atom bound to one of its three nitrogen atoms. The alkaline metal is preferably potassium.

The organometallic compounds according to this invention can be used in olefin polymerizations. Olefin monomer can be polymerized alone or with one more olefins and/or with other monomers. Preferable olefins are alfa-olefins, and most preferable is ethylene: homo or copolymers of ethylene are produced in huge amounts that the catalysts suitable to this kind of applications can be very valuable.

The organometallic compounds alone are usually not at all or only slightly active in polymerization reactions. The activity can be increased remarkably by using with them one or more cocatalysts which activates the organometallic to a suitable constitution to be able to catalyze the polymerization reaction. The most common cocatalyst in the art is methyl aluminoxane (MAO) which can appear in linear, cyclic or polymerized form. Formulas of different isomeric forms of aluminoxanes can be seen for instance in patent application FI 972230, which is herewith included as a reference.

Higher aluminoxanes having more than one carbon atoms in the alkyl group, e.g. 2 to 10 carbon atoms can be used. Also other kind of compounds than aluminoxane can be used although not often used in commercial scale. In this sense particularly boron compounds, e.g. boranes seem to be very interesting.

EXAMPLES

Synthesis and Polymerization Behaviour of 1,5,7-Triaza[4.4.0]Bicyclo-Dec-5-Enyl Zirconium and Titanium Complexes.

As said above, a preferable ligand L is 1,5,7-triaza[4.4.0] bicyclo-dec-5-enyl (TAB). The preparation synthesis of it and also the synthesis of the organometallic compound from the ligand is represented below as an example of the present invention.

First the syntheses of zirconium and titanium complexes with the 1,5,7-triaza[4.4.0]bicyclo-dec-5-enyl (TAB) ligand are described. The complexes were synthesized by reaction of TAB⁻K⁺ with $TiCl_4$, TAB with $ZrCl_4$ by using benzyl potassium in THF or in a direct exchange reaction between TAB and bis $(nBuCp)_2ZrCl_2$ in refluxing toluene The products were analysed with MS and NMR. The isolated complexes $(TAB)TiCl_3$, $(TAB)ZrCl_3$ and $(TAB)_2ZrCl_2$ were active catalysts in the homo-polymerization of ethylene with MAO/toluene in pentane. The activities were 167 kg $PE/g.Ti.h^{-1}$, 44 kg $PE/g.Zr.h^{-1}$ and 7 kg $PE/g.Zr.h^{-1}$, respectively. They were also active in the co-polymerization of ethylene with 1-hexene. The activities were 146 kg PE/g $Ti.h^{-1}$, 15 kg PE/g $Zr.h^{-1}$ and 9.0 kg $PE/g.Zr.h^{-1}$, respectively.

The following syntheses have been carried out successfully.

Equation 1. Synthesis of TAB⁻K⁺. (1)

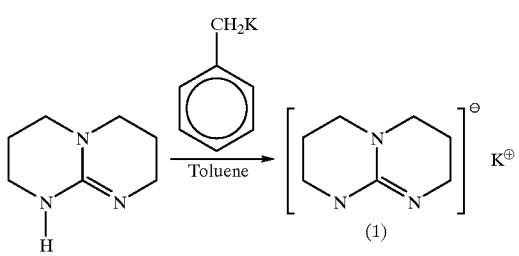

Equation 2. Synthesis of $(TAB)TiCl_3$. (2)

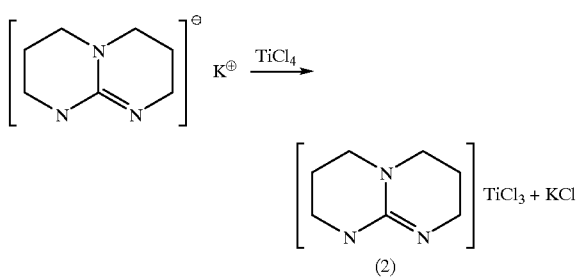

Equation 3. Synthesis $(TAB)ZrCl_3$. (3)

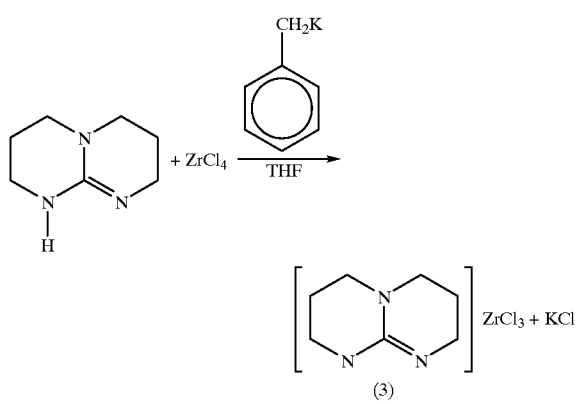

Equation 4. Synthesis of $(TAB)_3ZrCl$. (4)

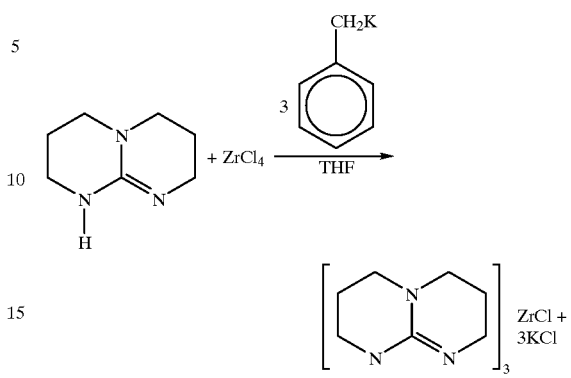

Equation 5. Synthesis of $(TAB)_2ZrCl_2$. (5)

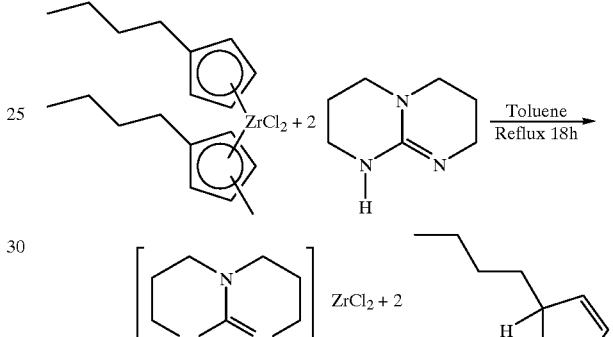

Equation 6. Second synthesis route to $(TAB)ZrCl_3$. (3)

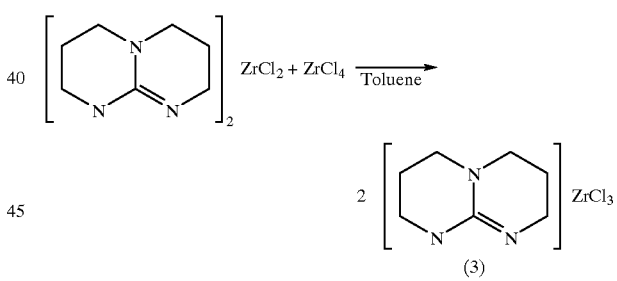

Experimental Section

General Considerations

All operations were carried out in argon or nitrogen atmosphere using a standard Schlenk flask, vacuum and dry box techniques. Solvents were dried with potassium benzophenone cetyl and distilled under argon prior to use. 1,5,7-triaza[4.4.0]bicyclo-dec-5-ene (Fluka), (nBuCp) $_2ZrCl_2$ (Witco) and $ZrCl_4$ (Aldrich) were used without further purification. Benzyl potassium was prepared according to literature (Schlosser, M. and Hartmann, *J. Angew. Chem* 1973, 85, 544–545). The ¹H-NMR spectra were recorded using JEOL JNM-EX 270 MHz FT NMR spectrometer with tetramethylsilane (TMS) as an internal reference. The MS spectra were recorded using VG Quadrupole TRIO 2 electronic ionization method and direct probe 70 eV spectrometer. The polymerization tests were carried out using MAO, 30% solution in toluene purchased from Albermarle Corp. Test polymerizations were carried out in pentane at 80° C. with no hydrogen present sing an Al/Zr ratio of 1000 unless otherwise stated. A Büchi 2 L stirred reactor with mantle heating was used for the polymerization tests.

Example 1

(1,5,7-triaza[4.4.0]bicyclo-dec-5-enyl)potassium (1), $C_7H_{12}KN_3$

Red solid benzyl potassium (9.6 g, 73.3 mmol) was added as a solid onto the solution of 1,5,7-triaza[4.4.0]bicyclo-dec-5-ene (10.2 g, 73.3 mmol) in 350 ml of dry toluene at −40° C. to obtain a red slurry. The temperature was allowed to warm to room temperature and the mixture stirred for 16 h at this temperature to obtain a white slurry. The solvents were removed in a vacuum and the product washed with 3×60 ml of ether and dried in a vacuum to obtain 10.1 g (78%) of white powder. $^1$H-NMR in THF-$d_8$; δ: 3.17 (t, 4H); 2.98 (t, 4H); 1.69 (t, 4H). The salt could not be analyzed with MS. Elemental analysis according to calculation: C 47.4%, H 6.8%, N 23.7%, K 22.1% and according to the practical analysis: C 46.0%, H 6.4%, N 23.1%.

Example 2

(1,5,7-triaza[4.4.0]bicyclo-dec-5-enyl)titanium Trichloride (2), $C_7H_{12}Cl_3N_3Ti$.

The potassium salt of 1,5,7-triaza[4.4.0]bicyclo-dec-5-ene (1), (1.0 g, 5.6 nmmol) in 50 ml toluene at −20° C. was addded as a slurry onto yellow solution of $TiCl_4$ (0.6 ml, 5.6 mmol) in 50 ml of toluene at −20° C. during one hour to obtain an orange slurry. The mixture was stirred 16 h at −15° C. to obtain a red solution with a lighter solid in it. The solid was filtrated off and washed with 3×20 ml of toluene. The filtrate was evaporated and dried in a vacuum yielding 0.6 g (36%) of yellow solid. $^1$H-NMR in $C_6D_6$; δ: 3.67 (t, 4H); 1.96. (t, 4H); 1.12 (t, 4H). $M^+$=292.4.

Example 3

(1,5,7-triaza[4.4.0]bicyclo-dec-5-enyl)zirconium Trichloride (3), $C_7H_{12}N_3ZrCl_3$ Alternative higher yielding (49%) and simpler route to (3) is described in the example 6. A solution of 1,5,7-triaza [4.4.0]bicyclo-dec-5-ene (1.7 g, 12 mmol) in THF (30 ml) at room temperature was added dropwise onto a white slurry of $ZrCl_4$ (2.8 g, 12 mmol) in THF (50 ml) at −78° C. during 30 min. The whitish mixture was stirred for 1 h at −40° C. A dark red solution of benzyl potassium (1.6 g, 12 mmol) in THF (50 ml) was then slowly added dropwise onto the reaction mixture at −78° C. during 30 min. The mixture was stirred overnight and the temperature allowed to warm to room temperature. After 18 h stir ring the solution had turned from red to a whitish cream. The mixture was filtrated and the clear yellow solution evaporated in a vacuum to give a yellowish solid, which was purified by dissolving it in toluene and filtrating the insolubilities off. After evaporation a brownish paste was obtained and analyzed with MS and $^1$H-NMR in THF-$d_8$. Yield 1.75 g, (43%). $^1$H-NMR; δ: 3.48 (t, 4H); 3.31 (t, 4H); 1.92 (t, 4H). $M^+$=335.8. Elemental analysis according to calculation: C 25.0%, H 3.6%, Cl 31.7%, N 31.7%, Zr 27.2% and according to the practical analysis: C 26.0%, H 3.7%, Cl 29.0%, N 12.5%.

Example 4

Tris(1,5,7-triaza[4.4.0]bicyclo-dec-5-enyl)zirconium Chloride (4), $C_{21}H_{36}N_9ZrCl$ A solution of 1,5,7-triaza[4.4.0]bicyclo-dec-5-ene (3.3 g, 24 mmol) in THF (50 ml) at room temperature was added dropwise onto a red solution of benzyl potassium (3.1 g, 24 mmol) in THF (50 ml) at −78° C. during 60 min to obtain a red solution. The mixture was stirred overnight and the temperature allowed to warm to room temperature. After 18 h stirring the solution had turned white. Solution was cooled to −78° C. and excess of solid $ZrCl_4$ (2.8 g, 12 mmol) was added in one portion to give a white slurry, which was stirred for 5 h at −78° C. The temperature was then allowed to warm to room temperature and the whitish mixture filtrated. The obtained clear yellow filtrate was evaporated in a vacuum to give 3.1 g (71.6%) of yellow solid, which was analysed with MS and $^1$H-NMR in THF-$d_8$. $^1$H-NMR; δ: 3.22 (t, 4H); 2.95 (t, 4H); 1.70 (t, 4H). $M^+$=541.3.

Example 5

Bis(1,5,7-triaza[4.4.0]bicyclo-dec-5-enyl)zirconium Dichloride (5), $C_{14}H_{24}N_6ZrCl_2$ Solid 1,5,7-triaza[4.4.0]bicyclo-dec-5-ene (3.45 g, 24.8 mmol) was added during five minutes onto a solution of bis-(nBuCp)$_2$ZrCl$_2$ (5.02 g, 12.4 mmol) in 200 ml of toluene at −30° C. resulting in a dark brown solution. The solution was allowed to warm to room temperature and then refluxed for 18 hours to give a whitish precipitate. The cooled mixture was filtrated, washed with 3×50 ml of toluene and dried in a vacuum to yield 5.1 g (94%) of grey-white powder. $M^+$=438.5. EA; C=39.0%, H=5.4%, N=17.5%. $^1$H-NMR spectrum in DMSO-$d_6$ (dissolution after 3 days) δ: 3.28 (t, 4H); 3.09 (t, 4H); 1.72 (t, 4H). Elemental analysis according to calculation: C 38.3%, H 5.5%, Cl 16.2%, N 19.2%, Zr 20.8% and according to the practical analysis: C 37.6%, H 5.4%, Cl 15.3%, N 18.6%.

Example 6

(1,5,7-triaza[4.4.0]bicyclo-dec-5-enyl)zirconium Trichloride (3), $C_7H_{12}N_3ZrCl_3$ Route 2. Solid $ZrCl_4$ (1.06 g, 4.56 mmol) was added into a white slurry of (5) (2.0 g, 4.56 mmol) in 150 ml of toluene at −60° C. during 10 minutes. The temperature was allowed to warm to room temperature. The resulting light brown mixture was then refluxed for 72 h. The cooled white-grey mixture was filtrated, washed with 3×30 ml of toluene and dried in a vacuum. The raw product was purified by hot soxhlet treatment (extraction) from boiling toluene. Yield 49%.

Test Polymerization Data

Polymerizations were carried out in a 2 l stainless steel autoclave reactor equipped with a paddle stirrer and continuous supply of ethylene. Hydrogen and comonomer, if used were fed to the reactor simultaneously with ethylene. MFR's of the produced polymers were measured according to the ISO-1133 method. GPC was used to determine the average molecular weights and molecular weight distributions of the produced polymers. Polymerization temperature was 80° C. and ethylene pressure 10 bar.

Abbreviations in the Following Tables

HOPO=homopolymerization
COPO=copolymerization
/H$_2$=with hydrogen added as chain transfer agent

TABLE 1

Homopolymerizations of ethylene with various TAB catalysts.
Polymerization temperature was 80° C. Ethylene pressure was 10 bar.

| Pol. Type | HOPO | HOPO | HOPO | HOPO |
|---|---|---|---|---|
| Cat. name | (TAB)ZrCl$_3$ (3) | (TAB)$_3$ZrCl (4) | (TAB)$_2$ZrCl$_2$ (5) | (TAB)TiCl$_3$ (2) |
| Comp. | C$_7$H$_{12}$Cl$_3$N$_3$Zr | C$_{21}$H$_{36}$N$_9$ZrCl | C$_{12}$H$_{24}$N$_6$ZrCl$_2$ | C$_7$H$_{12}$Cl$_3$N$_3$Ti |
| Comp. μmol | 7.56 | 10 | 10 | 10 |
| Al/metal | 500 | 500 | 500 | 1000 |
| Pentane ml | 1200 | 1200 | — | 1200 |
| Isobutane ml | — | — | 1200 | — |
| Yield g | 15 | 0 | 3 | 40 |
| Activity kgPO/gM h$^{-1}$ | 44 | 0 | 7 | 167 |

TABLE 2

Copolymerization and H$_2$/homopolymerization with (TAB)$_2$ZrCl$_2$ (5).

| Run type | HOPO | HOPO | COPO | HOPO/H$_2$ |
|---|---|---|---|---|
| Compound type | (TAB)$_2$ZrCl$_2$ | (TAB)$_2$ZrCl$_2$ | (TAB)$_2$ZrCl$_2$ | (TAB)$_2$ZrCl$_2$ |
| Comp. amount (μmol) | 10 | 10 | 10 | 10 |
| Al/metal | 500 | 1500 | 1000 | 1000 |
| Medium | Isobutane | Isobutane | Pentane | Pentane |
| Medium (ml) | 1200 | 1200 | 1200 | 1200 |
| Comonomer | — | — | 1-Hexene | — |
| Comonomer (ml) | — | — | 50 | — |
| Yield (g) | 3 | 6 | 4 | 1 |
| Activity (kg PE/g met.h$^{-1}$) | 7 | 13 | 9 | 2 |
| MFR$_{21}$ (g/10 min) | — | 0,09 | — | — |
| Crystallinity (%) | 53.4 | 54,5 | 27 | — |
| Tm ° C. | 136,7 | 135,8 | 122.9 | — |
| Mn | 125000 | 198000 | 29100 | — |
| Mw | 433000 | 477000 | 305000 | — |
| Mw/Mn | 3.5 | 2.4 | 10.5 | — |

TABLE 3

Test polymerization data of (TAB)TiCl$_3$. (2). Amount of the catalyst was 10 μmol. Al/metal ratio was 1000. Run temperature was 80° C. The polymerizations were carried out in 1200 ml of pentane. Ethylene pressure was 10 bar. Run time was 30 min.

| Run type | HOPO | HOPO/H$_2$ | COPO |
|---|---|---|---|
| Compound type | (TAB)TiCl$_3$ | (TAB)TiCl$_3$ | (TAB)TiCl$_3$ |
| Comp. amount (μmol) | 10 | 10 | 10 |
| Comonomer | — | — | 1-Hexene |
| Comonomer (ml) | — | — | 50 |
| Yield (g) | 40 | 18 | 35 |
| Activity (kg PE/g M h) | 167 | 75 | 146 |
| Activity (kg PE/mmol M h) | 8 | 3,6 | 7 |
| MFR$_{21}$ (g/10 min) | 0 | 0,3 | 0 |
| Comonomer (wt-%) | | | 1.8 |
| t-vinylene (C=C/1000 C) | 0 | 0 | 0.,01 |
| Vinyl | 0.38 | 0.93 | 0.35 |
| Vinylidene | 0.05 | 0.06 | 0.03 |
| Crystallinity (%) | 59.2 | 64.8 | 50.6 |
| Tm ° C. | 136.6 | 134.8 | 127.7 |

TABLE 4

Test polymerization data of (TAB)ZrCl$_3$ (3). The run temperature was 80° C., Al/metal ratio was 1000 and the ethylene pressure 10 bar. Polymerizations were carried out in pentane.

| Run type | HOPO | COPO | HOPO/H$_2$ |
|---|---|---|---|
| Compound type | (TAB)ZrCl$_3$ | (TAB)ZrCl$_3$ | (TAB)ZrCl$_3$ |
| Comp. amount (mmol) | 10 | 10 | 10 |
| Al/metal | 1000 | 1000 | 1000 |
| Comonomer | | 1-Hexene | |
| Comonomer (ml) | | 50 | |
| Yield estimate (g) | 8 | 7 | 5 |
| Activity (kg PE/g met.h) | 18 | 15 | 11 |
| Comonomer (wt-%) | | 2.6 | |
| Crystallinity (%) | 56.1 | 42,3 | 55.6 |
| Tm ° C. | 135.8 | 126.9 | 135 |
| Mn | 56800 | 20100 | 14900 |
| Mw | 623000 | 359000 | 430000 |
| Mw/Mn | 11 | 17.8 | 28.9 |

What is claimed is:

1. An organometallic compound comprising a central transition metal atom and a ligand coordinated thereto having a heteroatomic ring structure, of the formula (1)

$$L_nMX_{m-n} \quad (1)$$

Wherein at least one L denotes said ligand bound to M and includes a heterocyclic ring structure having at least two fused rings, containing at least three nitrogen atoms, of which three are being connected to the same carbon atom, one being common for said two fused rings and two occurring separately in each of the fused rings, M is the central transition metal atom and belongs to Groups IV, V or VI of the Periodic Table of the Elements, X is an organic group or a halide coordinated to said central transition metal atom M, m signifies the coordination (ligand) number of said transition metal atom M, and n signifies an integer from 1 to 10.

2. A compound according to claim 1, wherein the ligand L is a fused bicyclo group having three nitrogen atoms in their ring structure.

3. Compound according to claim 2 wherein the ligand L is a triaza bicycloalkenyl group.

4. A compound according to claim 3, wherein the ligand L is 1,5,7-triazabiscyclo-dec-5-enyl.

5. Compound according to any of claims 1 to 4 wherein M is titanium, zirconium, hafnium or chromium.

6. Compound according to claim 1 wherein two of the ligands L are bridged by a bivalent group.

7. Compound according to claim 6 wherein two of the ligands L are bridged by a substituted or non-substituted alkylene or silylene group having optionally one or more heteroatoms in the substituents or in the carbon and/or silicon chain.

8. Compound according claims 1 wherein the X group is a chloride group.

9. A compound according to claim 1, wherein the X group is a dialkyl amide.

10. Compound according to any of claim 1 wherein n>1 and a part of the ligands L is replaced by a substituted or unsubstituted cyclopentadienyl compound.

11. A compound according to claim 4, wherein the ligand is 1,5,7-triaza{4.4.0}bicyclo-dec-5-enyl.

12. A compound according to claim 9, wherein the X group is a dimethyl or diethyl amide group.

13. A method to prepare an organometallic compound comprising a central transition metal and a ligand coordinated thereto having a heteroatomic ring structure, wherein the compound consisting of the ligand which includes a heterocyclic ring structure having at least two fused rings, containing at least three nitrogen atoms, of which three are being connected to the same carbon atom, one being common for said two fused rings and two occuring separately in each of the fused rings, and a hydrogen atom bound to one of said three nitrogen atoms of said ligand, is reacted with a metallocene and/or a halide of said transition metal.

14. A method according to claim 13, wherein an alkaline metal salt of the ligand is reacted with a transition metal halide.

15. A method according to claim 14, wherein the alkaline metal salt of the ligand is prepared as follows:
first an alkaline metal salt of toluene is produced, and the salt is then reacted in toluene solution with said compound consisting of the ligand and a hydrogen atom bound to one of its three nitrogen atoms.

16. A method according to claim 14 or 15, wherein the alkaline metal is potassium.

17. A method according to claim 14, wherein the transition metal halide is chloride.

18. A process for the production of olefin polymers, wherein one or more olefins, optionally with other monomers is polymerized in the presence of a catalyst composition comprising one or several metallocene compounds according to claim 1 and a cocatalyst.

19. A process according to claim 18, wherein the cocatalyst comprises one or more aluminoxane compounds.

20. A process according to claim 19, wherein the cocatalyst is linear or cyclic methyl aluminoxane (MAO).

* * * * *